US010786144B2

(12) United States Patent
Sone (10) Patent No.: US 10,786,144 B2
(45) Date of Patent: Sep. 29, 2020

(54) ENDOSCOPE

(71) Applicant: OLYMPUS CORPORATION, Hachioji-shi, Tokyo (JP)

(72) Inventor: Nobuhiko Sone, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 365 days.

(21) Appl. No.: 15/956,202

(22) Filed: Apr. 18, 2018

(65) Prior Publication Data
US 2018/0228356 A1 Aug. 16, 2018

Related U.S. Application Data

(63) Continuation of application No. PCT/JP2016/078261, filed on Sep. 26, 2016.

(30) Foreign Application Priority Data

Oct. 20, 2015 (JP) .................. 2015-206571

(51) Int. Cl.
*A61B 1/07* (2006.01)
*A61B 1/06* (2006.01)
(Continued)

(52) U.S. Cl.
CPC .............. *A61B 1/07* (2013.01); *A61B 1/0019* (2013.01); *A61B 1/00096* (2013.01); *A61B 1/06* (2013.01);
(Continued)

(58) Field of Classification Search
CPC ..... A61B 1/0607; A61B 1/07; A61B 1/00096; A61B 1/0019; A61B 1/06; A61B 1/04;
(Continued)

(56) References Cited

U.S. PATENT DOCUMENTS 6,251,068 B1 * 6/2001 Akiba ................ A61B 1/00096
600/177

9,030,764 B2 * 5/2015 Asami .................... G02B 13/06
359/713
(Continued)

FOREIGN PATENT DOCUMENTS

JP          11342105 A      12/1999
JP        2000037345 A       2/2000
(Continued)

OTHER PUBLICATIONS

International Preliminary Report on Patentability (IPRP) (and English language translation thereof) dated May 3, 2018 issued in counterpart International Application No. PCT/JP2016/078261.
(Continued)

*Primary Examiner* — Timothy J Neal
*Assistant Examiner* — Jae Woo
(74) *Attorney, Agent, or Firm* — Holtz, Holtz & Volek PC (57) ABSTRACT

The endoscope includes an observing optical system having a magnified-observation function which enables a proximity observation by approximating an object, and at least three illuminating optical systems which are, a first illuminating optical system, a second illuminating optical system, and a third illuminating optical system. An amount of light of the first illuminating optical system which is at a distance nearest from the observing optical system, out of at least the three illuminating optical systems which are the first illuminating optical system, the second illuminating optical system, and the third illuminating optical system, is not more than half of an amount of light of the second illuminating optical system and the third illuminating optical system, and the endoscope satisfies the following conditional expressions (1'), (2'), (3), (4), (6), and (7).

$$0.5 < rd1/rd3 < 0.75 \quad (1')$$

$$0.5 < rd1/rd2 < 0.75 \quad (2')$$

$$0.3 < (rd2^2 \times LI1)/(rd1^2 \times LI2) < 1.2 \quad (3)$$

$$0.3 < (rd3^2 \times LI1)/(rd1^2 \times LI3) < 1.2 \quad (4)$$

(Continued)

| | |
|---|---|
| $1.05 < \theta 1/\theta 2 < 1.45$ | (6) |
| $1.05 < \theta 1/\theta 3 < 1.45$ | (7) |

2 Claims, 6 Drawing Sheets

(51) Int. Cl.
*A61B 1/00* (2006.01)
*A61B 1/04* (2006.01)
*G02B 23/24* (2006.01)
*G02B 13/04* (2006.01)

(52) U.S. Cl.
CPC ....... *G02B 23/243* (2013.01); *G02B 23/2469* (2013.01); *A61B 1/04* (2013.01); *G02B 13/04* (2013.01)

(58) Field of Classification Search
CPC ... G02B 23/243; G02B 23/2469; G02B 13/04
See application file for complete search history.

(56) References Cited

U.S. PATENT DOCUMENTS

| | | | | |
|---|---|---|---|---|
| 2005/0030639 | A1* | 2/2005 | Homma | G02B 15/177 359/676 |
| 2007/0103912 | A1* | 5/2007 | Namii | G02B 21/082 362/341 |
| 2013/0310649 | A1* | 11/2013 | Sone | G02B 23/2469 600/177 |
| 2015/0103418 | A1* | 4/2015 | Takato | G02B 23/243 359/754 |
| 2016/0256042 | A1* | 9/2016 | Takato | A61B 1/0638 |
| 2018/0228356 | A1* | 8/2018 | Sone | A61B 1/07 |

FOREIGN PATENT DOCUMENTS

| | | |
|---|---|---|
| JP | 2001346752 A | 12/2001 |
| JP | 2009183618 A | 8/2009 |
| JP | 2011098051 A | 5/2011 |
| WO | 2013035522 A1 | 3/2013 |
| WO | 2013080831 A1 | 6/2013 |
| WO | 2014132494 A1 | 9/2014 |
| WO | 2015107844 A1 | 7/2015 |

OTHER PUBLICATIONS

Chinese Office Action dated Jul. 11, 2019 (and English translation thereof) issued in counterpart Chinese Application No. 201680061799.2.

International Search Report (ISR) dated Nov. 15, 2016 issued in International Application No. PCT/JP2016/078261.

Written Opinion dated Nov. 15, 2016 issued in International Application No. PCT/JP2016/078261.

* cited by examiner

ENDOSCOPE

CROSS-REFERENCE TO RELATED APPLICATION

The present application is a continuation application of PCT/JP2016/078261 filed on Sep. 26, 2016 which is based upon and claims the benefit of priority from Japanese Patent Application No. 2015-206571 filed on Oct. 20, 2015; the entire contents of which are incorporated herein by reference.

BACKGROUND OF THE INVENTION

Field of the Invention

The present invention relates to an endoscope which includes illuminating optical systems and an observing optical system.

Description of the Related Art

So far, in an endoscope which enables proximity magnifying observation, as a distance between the endoscope and an object becomes close, an area on which illuminating light is to be irradiated with respect to an observing optical system, is concentrated at a peripheral area, and a brightness of a central area that is to be observed mainly, cannot be secured adequately. This is because, as the distance between the endoscope and an object becomes close, an effect of an arrangement of the observing optical system and the illuminating optical system has dominance over a light-distribution performance of the illuminating optical system. Therefore, in an endoscope that enables the proximity magnified observation in which the distance between the endoscope and an object is not more than 2 mm, for securing the brightness of the central area, an arrangement as in Japanese Patent Application Laid-open Publication No. 2001-346752 and an arrangement as in Japanese Patent Application Laid-open Publication No. 2000-37345 have been proposed.

SUMMARY OF THE INVENTION

An endoscope according to the present invention includes an observing optical system having a magnified-observation function, which enables a proximity observation by approximating an object, and at least three illuminating optical systems which are, a first illuminating optical system, a second illuminating optical system, and a third illuminating optical system, wherein an amount of light of the first illuminating optical system which is at a distance nearest from the observing optical system, out of at least the three illuminating optical systems which are the first illuminating optical system, the second illuminating optical system, and the third illuminating optical system, is not more than half of an amount of light of the second illuminating optical system and the third illuminating optical system, and the endoscope satisfies the following conditional expressions (1'), (2'), (3), (4), (6), and (7).

$$0.5 < rd1/rd3 < 0.75 \quad (1')$$

$$0.5 < rd1/rd2 < 0.75 \quad (2')$$

$$0.3 < (rd2^2 \times LI1)/(rd1^2 \times LI2) < 1.2 \quad (3)$$

$$0.3 < (rd3^2 \times LI1)/(rd1^2 \times LI3) < 1.2 \quad (4)$$

$$1.05 < \theta1/\theta2 < 1.45 \quad (6)$$

$$1.05 < \theta1/\theta3 < 1.45 \quad (7)$$

where, rd1 denotes a distance between a center of a lens disposed nearest to object in the observing optical system and a center of a lens disposed nearest to object in the first illuminating optical system, rd2 denotes a distance between the center of the lens disposed nearest to object in the observing optical system and a center of a lens disposed nearest to object in the second illuminating optical system, rd3 denotes a distance between the center of the lens disposed nearest to object in the observing optical system and a center of a lens disposed nearest to object in the third illuminating optical system, here, the distance rd1 is a value smaller than the distances rd2 and rd3, LI1 denotes the amount of light of the first illuminating optical system, LI2 denotes the amount of light of the second illuminating optical system, LI3 denotes the amount of light of the third illuminating optical system, θ1 denotes an angle when an amount of light emerged in a 0° direction is let to be 1 becomes 0.3 with respect to light-distributed emerged from the first illuminating optical system, θ2 denotes an angle when an amount of light emerged in the 0° direction is let to be 1 becomes 0.3 with respect to light-distributed emerged from the second illuminating optical system, and θ3 denotes an angle when an amount of light emerged in the 0° direction is let to be 1 becomes 0.3 with respect to light-distributed emerged from the third illuminating optical system.

DETAILED DESCRIPTION OF THE INVENTION

Endoscope according to embodiments of the present invention will be described below by referring to the accompanying diagrams. However, the present invention is not restricted to the embodiments described below.

First Embodiment

Figure 1A:
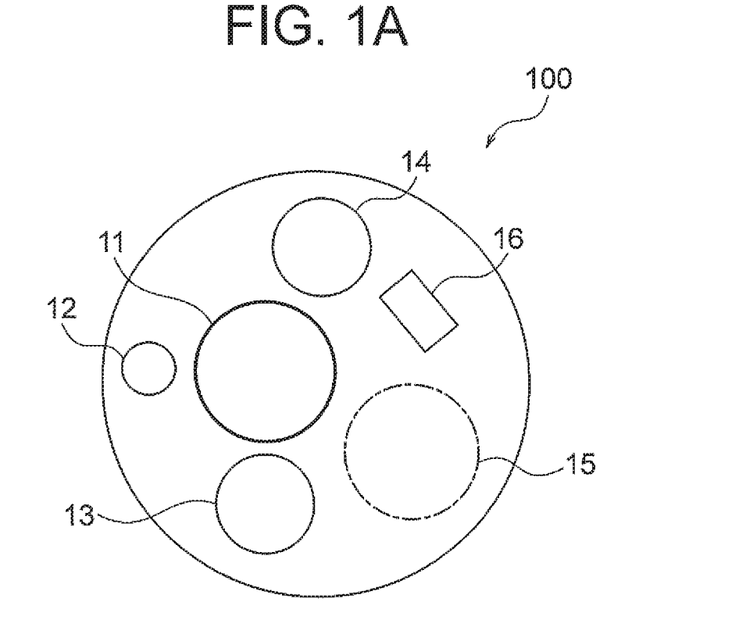
FIG. 1A is a diagram showing an arrangement of a front-end portion of an endoscope according to a first embodiment.
Figure 1B:
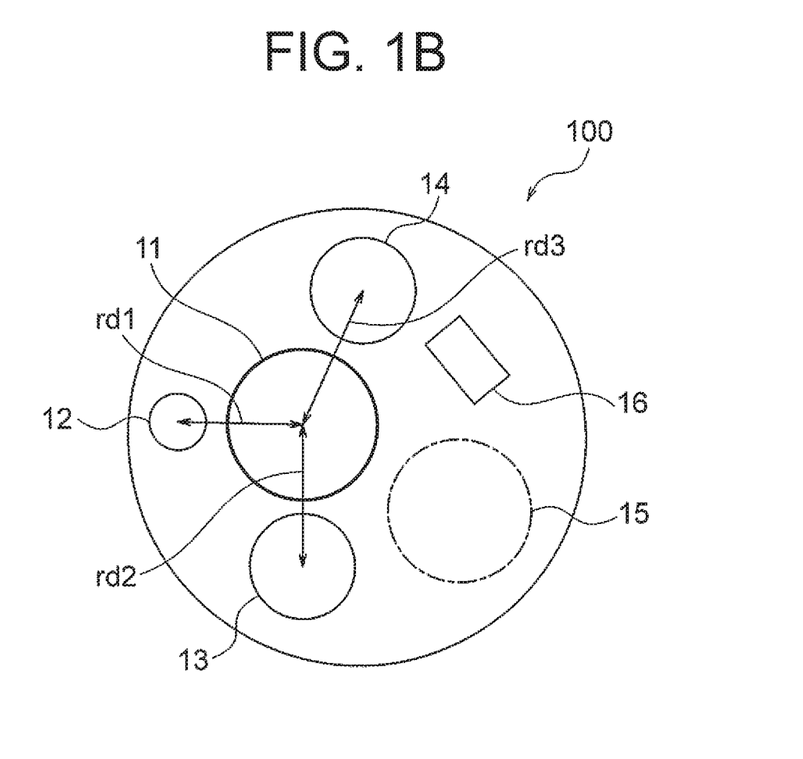
FIG. 1B is another diagram showing an arrangement of the front-end portion of the endoscope according to the first embodiment.

FIG. 1A and FIG. 1B are diagrams showing an arrangement of a front-end portion of an endoscope 100 according to a first embodiment.

The present embodiment is the endoscope 100 which includes an observing optical system 11 having a magnified-observation function, which enables a proximity observation by approximating an object, and at least three illuminating optical systems which are, a first illuminating optical system 12, a second illuminating optical system 13, and a third illuminating optical system 14, wherein an amount of light of the first illuminating optical system 12 which is at a distance nearest from the observing optical system 11, out of at least the three illuminating optical systems which are the first illuminating optical system 12, the second illuminating optical system 13, and the third illuminating optical system 14, is not more than half of an amount of light of the second illuminating optical system 13 and the third illuminating optical system 14, and the endoscope satisfies the following conditional expressions (1) and (2).

$$0.4 < rd1/rd3 < 0.8 \quad (1)$$

$$0.4 < rd1/rd2 < 0.8 \quad (2)$$

where, $rd1$ denotes a distance between a center of a lens disposed nearest to object in the observing optical system 11 and a center of a lens disposed nearest to object in the first illuminating optical system 12, $rd2$ denotes a distance between the center of the lens disposed nearest to object in the observing optical system 11 and a center of a lens disposed nearest to object in the second illuminating optical system 13, and $rd3$ denotes a distance between the center of the lens disposed nearest to object in the observing optical system 11 and a center of a lens disposed nearest to object in the third illuminating optical system 14, and here, the distance $rd1$ is a value smaller than the distances $rd2$ and $rd3$.

A treatment tool is to be inserted into and removed from a channel 15. A nozzle 16 injects cleaning water for cleaning dirt etc. adhered to a lens nearest to object in the observing optical system 11.

Reasons for and effects of adopting such arrangement in the present embodiment will be described below. At the time of proximity observation, a direction in which the illuminating optical system is disposed becomes bright with respect to the observing optical system 11. Therefore, an area in which the illuminating optical system has not been disposed becomes dark. For making the brightness of illumination uniform, an improvement is possible by disposing the illuminating optical systems uniformly. Here, in the endoscope, it is necessary to dispose the channel 15 for insertion and removal of a treatment tool, and the nozzle 16 which supplies water for removing the dirt adhered to a lens surface of the observing optical system 11.

When disposing the channel 15 and the nozzle 16 is taken into consideration, there is a problem of a diameter of a front end of the endoscope 100 becoming large. Moreover, at the time of proximity observation, when the arrangement of the illuminating optical systems is optimized, in a normal observation, phenomena such as a flare and a halation, which are not desirable optically, are susceptible to occur.

Moreover, not only the arrangement of the illuminating optical systems but also a difference in the amount of light of each of the illuminating optical systems at the time of proximity observation also has a significant effect on light-distribution characteristics. For instance, when only one illuminating optical system is disposed at a distance near from the observing optical system 11, an effect of illumination by this illuminating optical system is predominant, and the other directions become dark.

Moreover, in a case in which the distance between the observing optical system and the plurality of illuminating optical systems is same, when there is a difference in amount of light of each of the plurality of illuminating optical systems, only a direction of a brighter illuminating optical system becomes bright, and the other directions become dark.

Therefore, in the present embodiment, for making the brightness uniform at the time of proximity observation and the normal observation, three or more than three illuminating optical systems are used. The endoscope 100 includes at least three illuminating optical systems, or in other words, the first illuminating optical system 12, the second illuminating optical system 13, and the third illuminating optical system 14.

Firstly, the amount of light of the first illuminating optical system 12 is let to be half of the amount of light of the second illuminating optical system 13 and the third illuminating optical system 14 which are the other illuminating optical systems. Accordingly, the optimum illumination arrangement has been made possible without making a diameter of the endoscope 100 large, while maintaining an adequate amount of light necessary at the time of proximity observation.

The second illuminating optical system 13 and the third illuminating optical system 14, which are the other two illuminating optical systems, are arranged to make the light distribution appropriate at the time of normal observation, while assisting the illumination at the time of proximity observation. Accordingly, it is possible to reduce an occurrence of problems such as the flare and the halation.

Moreover, by satisfying conditional expressions (1) and (2), it is possible to let the second illuminating optical system 13 and the third illuminating optical system 14 having the amount of light smaller than the amount of light of the first illuminating optical system 12, to be specialized for making the brightness at the time of proximity observation uniform.

When a value falls below a lower limit value of conditional expressions (1) and (2), the brightness at the time of proximity observation becomes uniform, but there is an increased risk of occurrence of flare which occurs due to light of the first illuminating optical system 12 disposed near the observing optical system 11 being incident directly on the observing optical system 11.

When an upper limit value of conditional expressions (1) and (2) is exceeded, a contribution of the other illuminating optical systems 13 and 14 at the time of proximity observation increases, and uniform brightness cannot be secured.

It is desirable to satisfy the following conditional expressions (1') and (2') instead of conditional expressions (1) and (2) respectively.

$$0.5 < rd1/rd3 < 0.75 \quad (1')$$

$$0.5 < rd1/rd2 < 0.75 \quad (2')$$

Moreover, when the amount of light of the first illuminating optical system 12 near the observing optical system 11 is large, there is an increased risk of the flare occurring due to light entering directly into the observing optical system 11. Therefore, it is desirable that the amount of light of the first illuminating optical system 12 which is let to be specialized for the proximity observation is small. For instance, it is more preferable that the amount of light of the first illuminating optical system 12 is one third of the amount of light of the second illuminating optical system 13 and the third illuminating optical system 14. Furthermore, it is even more preferable that the amount of light of the first illuminating optical system 12 is one fourth of the amount of light of the second illuminating optical system 13 and the third illuminating optical system 14.

Second Embodiment

Moreover, it is desirable that an endoscope according to a second embodiment satisfies the following conditional expressions (3) and (4).

$$0.3 < (rd2^2 \times LI1)/(rd1^2 \times LI2) < 1.2 \quad (3)$$

$$0.3 < (rd3^2 \times LI1)/(rd1^2 \times LI3) < 1.2 \quad (4)$$

where,

LI1 denotes the amount of light of the first illuminating optical system 12, LI2 denotes the amount of light of the second illuminating optical system 13, and LI3 denotes the amount of light of the third illuminating optical system 14.

Reasons for and effects of adopting such arrangement in the present embodiment will be described below.

For carrying out the proximity observation favorably, a balance of the distance and the amount of light of the first illuminating optical system 12 disposed at a position (distance) nearest to the observing optical system 11 and the second illuminating optical system 13 and the third illuminating optical system 14 becomes notably significant. Particularly, in the proximity observation, since an object to be observed closely is brought at a center of a screen in many cases, it becomes significant to increase the brightness of a central area of the screen. However, when the balance of the distance and the amount of light is inappropriate, only a certain direction becomes bright. Consequently, only that direction becomes bright, and as a result, the central area of the screen does not become bright. Therefore, it is desirable to satisfy conditional expressions (3) and (4).

When a value falls below a lower limit value of conditional expressions (3) and (4), an effect of the amount of light of the second illuminating optical system 13 and the third illuminating optical system 14 becomes excessively strong. Consequently, an effect of illumination by the illuminating optical system 12 which is near the observing optical system 11 cannot be exerted adequately, and the central portion does not become bright.

When an upper limit value of conditional expressions (3) and (4) is exceeded, only the effect of the first illuminating optical system 12 which is at a close distance from the observing optical system 11 becomes excessively strong. Consequently, the effect of the second illuminating optical system 13 and the third illuminating optical system 14 cannot be exerted adequately, and the central portion does not becomes bright adequately.

It is desirable to satisfy the following conditional expressions (3') and (4') instead of conditional expressions (3) and (4).

$$0.5 < (rd2^2 \times LI1)/(rd1^2 \times LI2) < 1.1 \quad (3')$$

$$0.5 < (rd3^2 \times LI1)/(rd1^2 \times LI3) < 1.1 \quad (4')$$

Third Embodiment

Moreover, it is desirable that an endoscope according to a third embodiment satisfies the following conditional expression (5).

$$1.1 < w(\text{wide})/w(\text{tele}) < 3 \quad (5)$$

where, w(wide) denotes an angle of view at the time of normal observation of the observing optical system 11, and w(tele) denotes an angle of view at the time of proximity magnified observation of the observing optical system 11.

Reasons for and effects of adopting such arrangement in the present embodiment will be described below.

Particularly, for improving the light-distribution characteristics at the time of proximity observation, not only an effect of the illuminating optical system but also an effect of the observing optical system 11 cannot be ignored. At the time of proximity observation, the distance between the observing optical system 11 and the object is close. Therefore, light of the plurality of illuminating optical systems is spread adequately, and is irradiated to the object before becoming uniform. Under such circumstances and when an angle of view of the observing optical system 11 is wide, a peripheral area of a screen where the illuminating optical system is disposed, becomes particularly bright. As a result, the brightness of at a central area of the screen becomes dark, and an observation performance is degraded. Therefore, it is desirable to satisfy conditional expression (5).

When a value falls below a lower limit value of conditional expression (5), the angle of view at the time of proximity observation becomes excessively wide, and it is not possible to carry out favorable observation.

When an upper limit value of conditional expression (5) is exceeded, either the brightness at the central area of the screen is improved or an observation range is narrowed, and therefore it is not desirable.

Fourth Embodiment

Moreover, it is desirable that an endoscope according to a fourth embodiment satisfies the following conditional expressions (6) and (7).

$$1.05 < \theta1/\theta2 < 1.45 \quad (6)$$

$$1.05 < \theta1/\theta3 < 1.45 \quad (7)$$

where,

θ1 denotes an angle when an amount of light emerged in a 0° direction is let to be 1 becomes 0.3 with respect to light-distributed emerged from the first illuminating optical system 12, θ2 denotes an angle when an amount of light emerged in the 0° direction is let to be 1 becomes 0.3 with respect to light-distributed emerged from the second illuminating optical system 13, and θ3 denotes an angle when an amount of light emerged in the 0° direction is let to be 1 becomes 0.3 with respect to light-distributed emerged from the third illuminating optical system 14.

Reasons for and effects of adopting such arrangement in the present embodiment will be described below.

When a peripheral light distribution of the first illuminating optical system 12 nearest to the observing optical system 11 is made large, it is possible to make a screen effectively bright at the time of proximity observation.

However, when the light-distribution performance of the first illuminating optical system 12 is improved excessively, the first illuminating optical system 12 being close to the observing optical system 11, there is an increased risk of the flare occurring due to light entering directly into the observing optical system 11. Moreover, at the time of normal observation, when the light distribution of the illuminating optical system is excessively wide, illuminating light of a distant object becomes dark, and there is a problem of degrading of the observation performance.

Therefore, it is desirable to take a balance of the light-distribution performance of each of the illuminating optical systems 12, 13, and 14, and to satisfy conditional expressions (6) and (7).

When a value falls below a lower limit value of conditional expressions (6) and (7), a contribution of the illuminating optical system disposed at a distance near from the observing optical system 11 is lowered at the time of proximity observation, and the observation performance is degraded.

When an upper limit value of conditional expressions (6) and (7) is exceeded, the observation at the time of proximity observation is improved, but the risk of occurrence of the flare increases.

It is desirable to satisfy the following conditional expressions (6') and (7') instead of conditional expressions (6) and (7).

$$1.1 < \theta1/\theta2 < 1.3 \quad (6')$$

$$1.1 < \theta1/\theta3 < 1.3 \quad (7')$$

Next, examples and numerical examples of the endoscope will be described below.

Figure 2A:
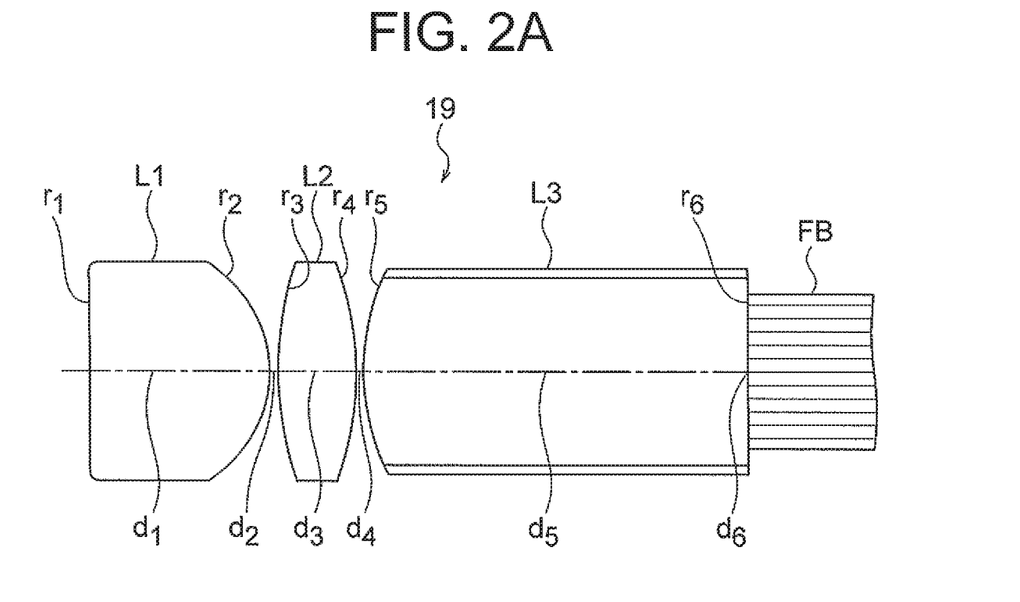
FIG. 2A is a cross-sectional view of a lens arrangement of an illuminating optical system.

FIG. 2A is a cross-sectional view showing a lens arrangement of an illuminating optical system 19. The illuminating optical system 19 includes in order from an object side, a planoconvex positive lens L1, a biconvex positive lens L2, a glass rod including a core and a clad, and a light guiding fiber FB. An arrangement is made such that a constant light distribution is achieved by refracting or reflecting light emerged from the light guiding fiber FB at each lens.

Figure 2B:
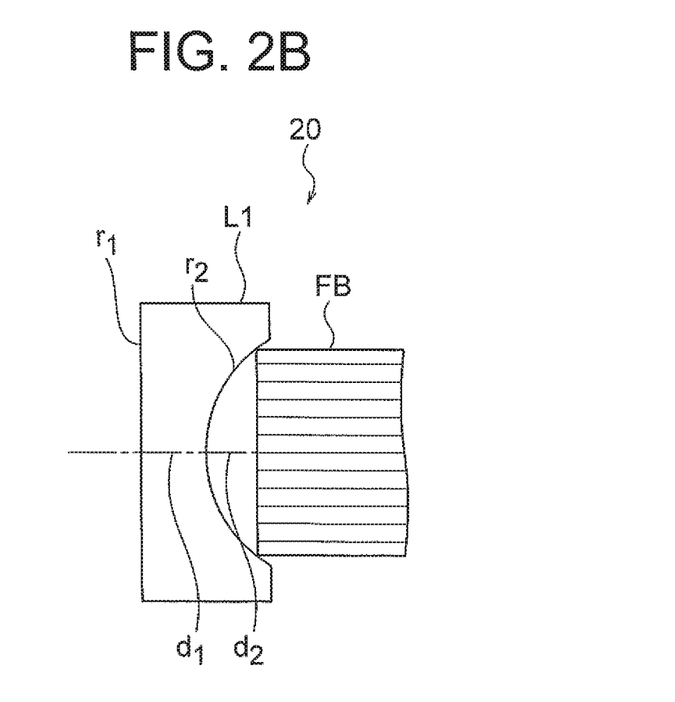
FIG. 2B is a cross-sectional view of a lens arrangement of another illuminating optical system.

FIG. 2B is a cross-sectional view showing a lens arrangement of another illuminating optical system 20. The illuminating optical system 20 includes in order from an object side, a planoconcave negative lens L1 and a light guiding fiber FB.

Figure 3:
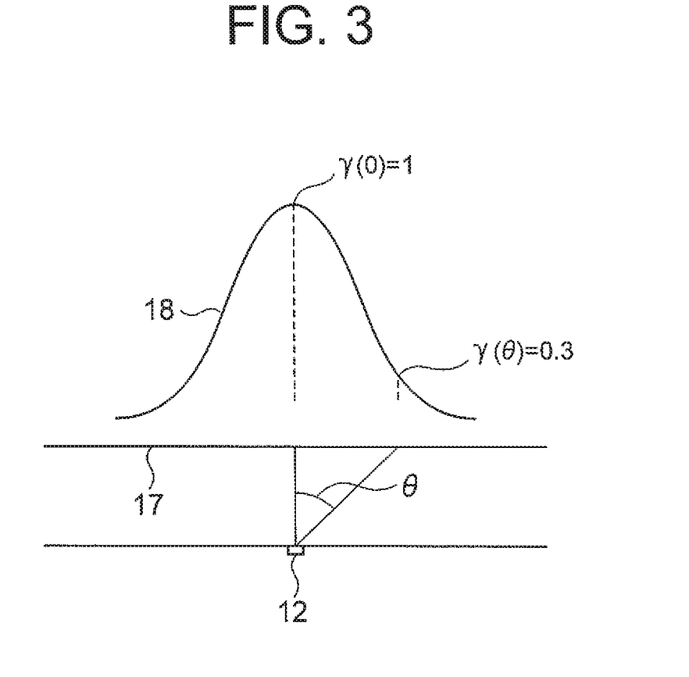
FIG. 3 is a diagram showing a light distribution with respect to a flat surface away by a distance 70 mm, by a first illuminating optical system.

FIG. 3 is a diagram showing light-distribution characteristics by the first illuminating optical system 12, for a flat surface away at a distance 70 mm. Light emerged from the first illuminating optical system 12 has a light distribution 18 with respect to a flat surface 17. Here, when an upward direction of a paper surface is let to be 0° in FIG. 3, the brightness at a position 0° is to be let to be γ(0)=1. Moreover, an angle in a clockwise direction is to be measured, and at this angle, an angle at which the brightness becomes 0.3 is to be defined as an angle θ. The light distribution being symmetrically shaped, the angle θ may be measured in a counterclockwise direction.

Moreover, light-distribution characteristics by the second and third illuminating optical systems 13 and 14 may be regarded similarly as the case of the first illuminating optical system 12. Furthermore, an integral value from 80° to −80° of this light-distribution characteristic is to be defined as an amount of light of the illuminating optical system.

A light guiding fiber FB used in examples, also has a light distribution characteristic $\gamma_{LG}$ as shown in table 1.

TABLE 1

| Angle | $\gamma_{LG}$ |
|---|---|
| 0 | 1.00 |
| 5 | 0.97 |
| 10 | 0.94 |
| 15 | 0.85 |
| 20 | 0.67 |
| 25 | 0.46 |
| 30 | 0.27 |
| 35 | 0.13 |
| 40 | 0.05 |
| 45 | 0.01 |
| 50 | 0.00 |

Numerical data for an illuminating optical system of each example is shown below. In surface data, r denotes a radius of curvature of each lens surface, d denotes a distance between two lens surfaces, nd denotes a refractive index for a d-line of each lens, and νd denotes Abbe's number for each lens. Furthermore, a distance between surfaces of the glass road and the light guiding fiber is let to be 0, and an area of an object-side end surface of the light guiding fiber FB is denoted by S.

An illuminating optical system A has an arrangement including three negative lenses and a light guiding fiber FB as shown in FIG. 2A, and numerical data for the illuminating optical system A is shown below.

Numerical Example 1

Unit mm
(Illuminating optical system A)
Surface data

| Surface number | r | d | nd |
|---|---|---|---|
| Object plane | ∞ | ∞ | |
| 1 | ∞ | 0.68 | 1.883 |
| 2 | −0.504 | 0.03 | |
| 3 | 1.29 | 0.3 | 1.883 |
| 4 | −1.29 | 0.03 | |
| 5 | 0.952 | 1.45 | 1.734 |
| 6 | ∞ | 0 | |
| FB | ∞ | 0.374(S) | |

An illuminating optical system B has an arrangement including one negative lens and a light guiding fiber FB as shown in FIG. 2B, and numerical data for the illuminating optical system B is shown below.

Numerical Example 2

Unit mm
(Illuminating optical system B)
Surface data

| Surface number | r | d | nd |
|---|---|---|---|
| Object plane | ∞ | ∞ | |
| 1 | ∞ | 0.36 | 1.883 |
| 2 | 0.76 | 0.37 | |
| FB | ∞ | 1.431(S) | |

An illuminating optical system C has an arrangement including three negative lenses and a light guiding fiber FB as shown in FIG. 2A, and numerical data for the illuminating optical system C is shown below.

Numerical Example 3

Unit mm
(Illuminating optical system C)
Surface data

| Surface number | r | d | nd |
|---|---|---|---|
| Object plane | ∞ | ∞ | |
| 1 | ∞ | 1.3 | 1.883 |
| 2 | −2 | 0.04 | |
| 3 | 2 | 0.75 | 1.883 |
| 4 | −2 | 0.05 | |
| 5 | 1.906 | 2.9 | 1.734 |
| 6 | ∞ | 0 | |
| FB | ∞ | 1.431(S) | |

An illuminating optical system D has an arrangement including three negative lenses and a light guiding fiber FB as shown in FIG. 2A, and numerical data for the illuminating optical system D is shown below.

Numerical Example 4

Unit mm
(Illuminating optical system D)
Surface data

| Surface number | r | d | nd |
|---|---|---|---|
| Object plane | ∞ | ∞ | |
| 1 | ∞ | 0.41 | 1.883 |
| 2 | −0.510 | 0 | |
| 3 | 0.536 | 0.325 | 1.883 |
| 4 | −0.536 | 0 | |
| 5 | 0.859 | 0.925 | 1.648 |
| 6 | ∞ | 0 | |
| FB | ∞ | 0.159(S) | |

An illuminating optical system E has an arrangement including one negative lens and a light guiding fiber FB as shown in FIG. 2B, and numerical data for the illuminating optical system E is shown below.

Numerical Example 5

Unit mm
(Illuminating optical system E)
Surface data

| Surface number | r | d | nd |
|---|---|---|---|
| Object plane | ∞ | ∞ | |
| 1 | ∞ | 0.3 | 1.883 |
| 2 | 0.7 | 0.21 | |
| FB | ∞ | 0.785(S) | |

An illuminating optical system F has an arrangement including one negative lens and a light guiding fiber FB as shown in FIG. 2B, and numerical data for the illuminating optical system F is shown below.

Numerical Example 6

Unit mm
(Illuminating optical system F)
Surface data

| Surface number | r | d | nd |
|---|---|---|---|
| Object plane | ∞ | ∞ | |
| 1 | ∞ | 0.3 | 1.883 |
| 2 | 0.56 | 0.3 | |
| FB | ∞ | 0.785(S) | |

Flat-surface light-distribution characteristics and an amount of light for the illuminating optical systems A to F having the abovementioned arrangement are shown in table 2 below. In the table, an 'Ill. A' denotes the illuminating optical system A. Similarly, Ill. B to F denote the illuminating optical systems B to F respectively. For the light distribution characteristics, a numerical value when the brightness with respect to 0° of the brightest illuminating optical system C is let to be 1 is indicated. Similar is true for the amount of light

TABLE 2

| Angle | Ill.A | Ill.B | Ill.C | Ill.D | Ill.E | Ill.F |
|---|---|---|---|---|---|---|
| 0 | 0.170 | 0.806 | 1.000 | 0.107 | 0.686 | 0.439 |
| 5 | 0.167 | 0.791 | 0.980 | 0.105 | 0.673 | 0.431 |
| 10 | 0.161 | 0.752 | 0.939 | 0.100 | 0.640 | 0.409 |
| 15 | 0.152 | 0.687 | 0.867 | 0.093 | 0.585 | 0.374 |
| 20 | 0.140 | 0.605 | 0.774 | 0.083 | 0.515 | 0.329 |
| 25 | 0.125 | 0.513 | 0.671 | 0.072 | 0.436 | 0.279 |
| 30 | 0.108 | 0.417 | 0.561 | 0.060 | 0.353 | 0.226 |
| 35 | 0.090 | 0.325 | 0.452 | 0.048 | 0.262 | 0.176 |
| 40 | 0.073 | 0.237 | 0.350 | 0.036 | 0.174 | 0.130 |
| 45 | 0.055 | 0.152 | 0.255 | 0.026 | 0.104 | 0.091 |
| 50 | 0.039 | 0.087 | 0.172 | 0.017 | 0.057 | 0.060 |
| 55 | 0.025 | 0.045 | 0.104 | 0.010 | 0.027 | 0.034 |
| 60 | 0.014 | 0.020 | 0.056 | 0.006 | 0.012 | 0.017 |
| 65 | 0.007 | 0.008 | 0.025 | 0.003 | 0.004 | 0.007 |
| 70 | 0.003 | 0.003 | 0.008 | 0.001 | 0.001 | 0.003 |
| 75 | 0.001 | 0.001 | 0.002 | 0.000 | 0.000 | 0.001 |
| 80 | 0.000 | 0.000 | 0.000 | 0.000 | 0.000 | 0.000 |
|  | 46.2 | 39.7 | 42.6 | 41.9 | 38.0 | 39.8 |
| Light amount | 0.18 | 0.76 | 1.00 | 0.11 | 0.63 | 0.42 |

In the examples described below, the illuminating optical systems having an arrangement including lenses and a light guiding fiber have been described. However, it may be an LED for instance, provided that it is an illuminating optical system having a performance as shown in table 2.

Next, an observing optical system 21 will be described below.

Figure 4A:
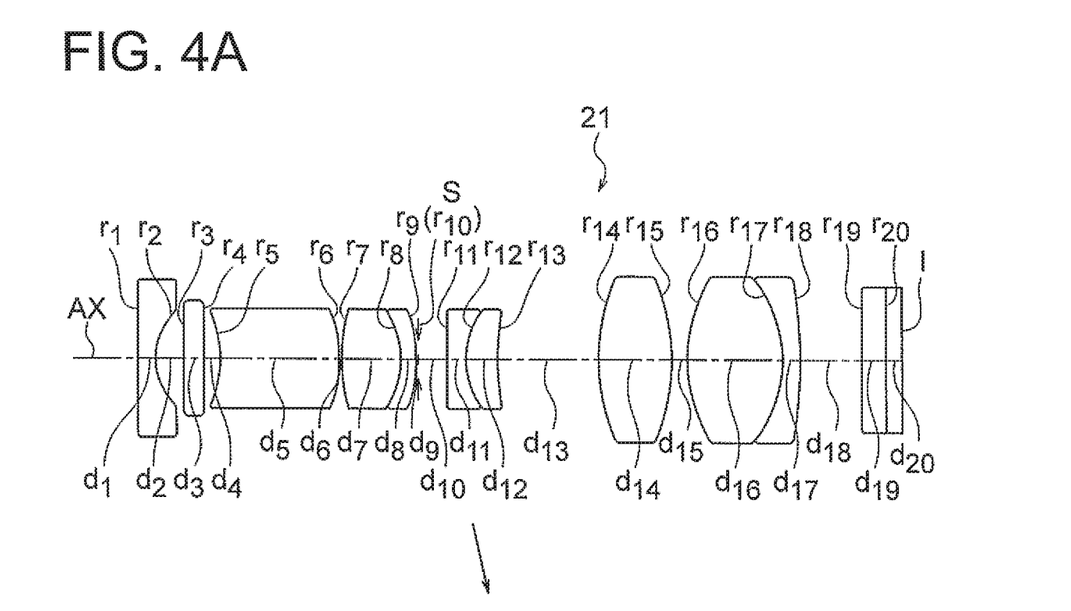
FIG. 4A is a cross-sectional view of a lens arrangement in a wide-angle end (wide) state of an observing optical system.
Figure 4B:
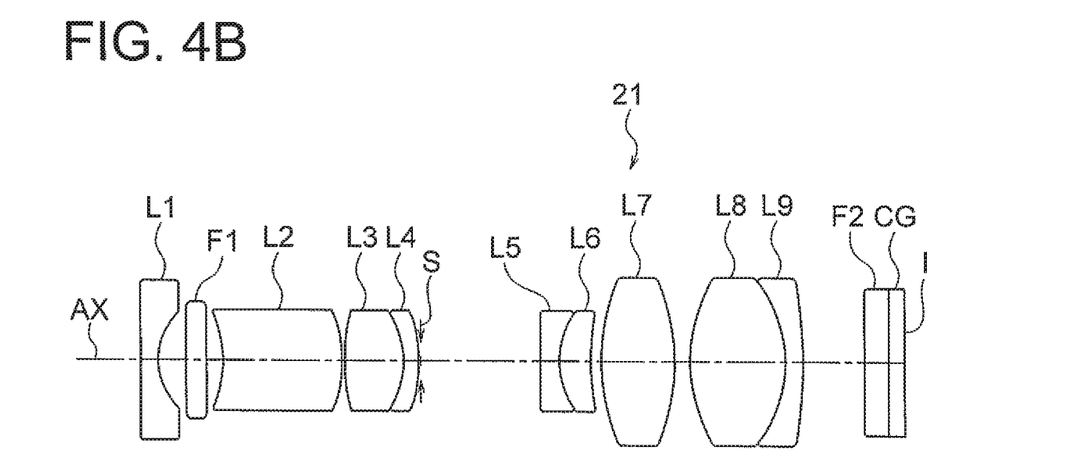
FIG. 4B is a cross-sectional view of a lens arrangement in a telephoto end (tele) state of the observing optical system.

FIG. 4A is a cross-sectional view of a lens arrangement in a wide-angle end (wide) state of the observing optical system 21. FIG. 4B is a cross-sectional view of a lens arrangement in a telephoto end (tele) state of the observing optical system 21.

The observing optical system 21 includes in order from an object side, a planoconcave negative lens L1, a plane parallel plate F1, a negative meniscus lens L2 having a convex surface directed toward an image side, a biconvex positive lens L3, a negative meniscus lens L4 having a convex surface directed toward the image side, an aperture stop S, a planoconcave negative lens L5, a positive meniscus lens L6 having a convex surface directed toward the object side, a biconvex positive lens L7, a biconvex positive lens L8, a negative meniscus lens L9 having a convex surface directed toward the image side, a plane parallel plate F2, and a plane parallel plate CG. Here, the biconvex positive lens L3 and the negative meniscus lens L4 are cemented. Moreover, the planoconcave negative lens L5 and the positive meniscus lens L6 are cemented. Also, the biconvex positive lens L8 and the negative meniscus lens L9 are cemented.

The plane parallel plate F2 is a cover glass, and the plane parallel plate CG is a glass encapsulating a CCD (charge coupled device). Moreover, by moving the planoconcave negative lens L5 and the positive meniscus lens L6, it is possible to change the state from the wide-angle end state to the telephoto end state.

Furthermore, an observing optical system 22 will be described below.

Figure 5A:
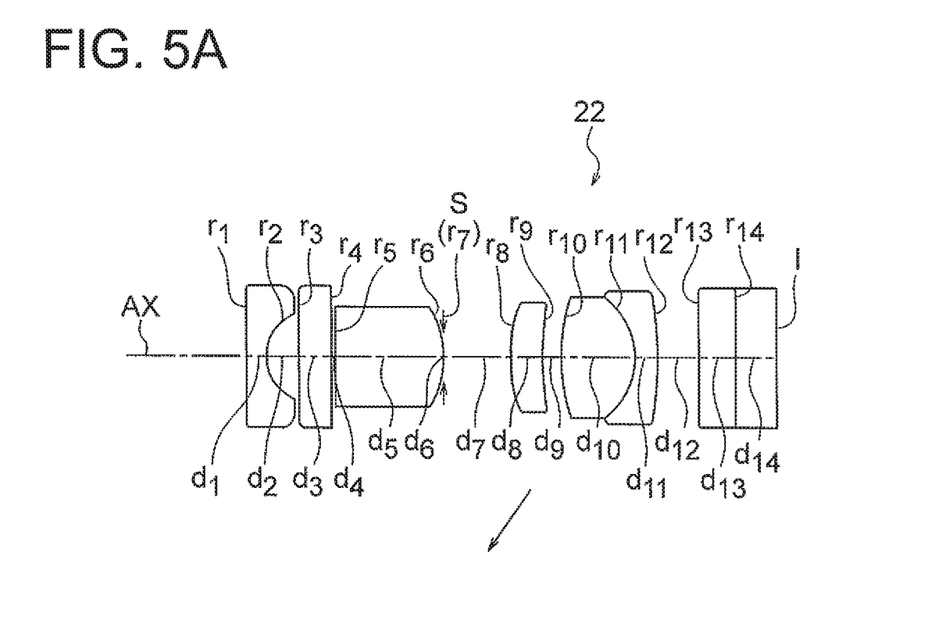
FIG. 5A is a cross-sectional view of a lens arrangement in a wide-angle end (wide) state of another observing optical system.
Figure 5B:
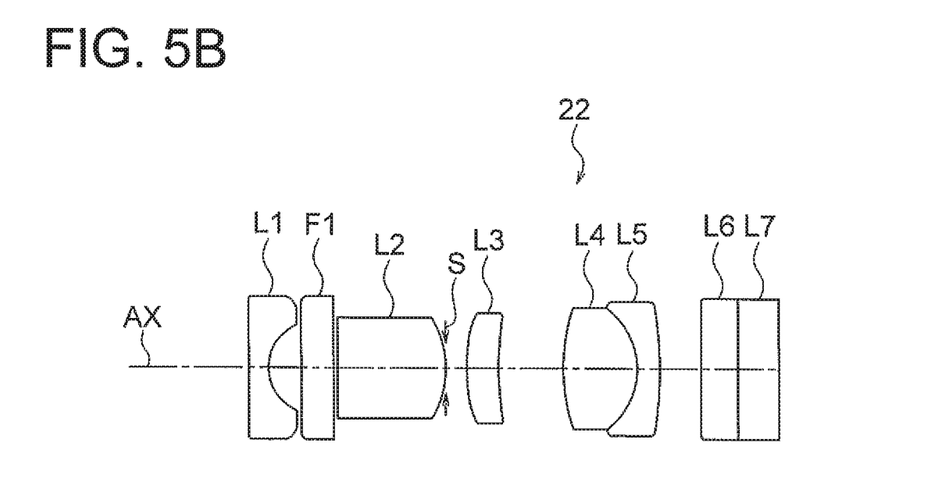
FIG. 5B is a cross-sectional view of a lens arrangement in a telephoto-end (tele) state of the another observing optical system.

FIG. 5A is a cross-sectional view of a lens arrangement in a wide-angle end (wide) state of the observing optical system 22. FIG. 5B is a cross-sectional view of a lens arrangement in a telephoto end (telephoto) state of the observing optical system 22.

The observing optical system 22 includes in order from an object side, a planoconcave negative lens L1, a plane parallel plate F1, a biconvex positive lens L2, an aperture stop S, a positive meniscus lens L3 having a convex surface directed toward the object side, a biconvex positive lens L4, a negative meniscus lens L5 having a convex surface directed toward an image side, a plane parallel plate F2, and a plane parallel plate CG. Here, the biconvex positive lens L4 and the negative meniscus lens L5 are cemented.

The plane parallel plate F2 is a cover glass, and the plane parallel plate CG is a glass encapsulating a CCD. Moreover, by moving the biconvex positive lens L4 and the negative meniscus lens L5, it is possible to change the state from the wide-angle end state to the telephoto end state.

An observing optical system A has an arrangement as shown in FIG. 4A and FIG. 4B, and numerical data for the observing optical system A is shown below.

Numerical Example 7

Unit mm
(Observing optical system A)

Surface data

| Surface number | r | d | nd | vd |
|---|---|---|---|---|
| Object plane | ∞ | variable(d0) | | |
| 1 | ∞ | 0.280 | 1.883 | 40.76 |
| 2 | 1.091 | 0.429 | | |
| 3 | ∞ | 0.325 | 1.494 | 75.00 |
| 4 | ∞ | 0.270 | | |
| 5 | −1.830 | 1.866 | 1.517 | 52.43 |
| 6 | −2.054 | 0.030 | | |
| 7 | 3.272 | 0.937 | 1.581 | 40.75 |
| 8 | −1.493 | 0.250 | 1.959 | 17.47 |

-continued

Unit mm
(Observing optical system A)

| | | | | |
|---|---|---|---|---|
| 9 | −2.510 | 0.030 | | |
| 10(Stop) | ∞ | variable(d10) | | |
| 11 | ∞ | 0.300 | 1.755 | 52.32 |
| 12 | 1.307 | 0.499 | 1.648 | 33.79 |
| 13 | 3.823 | variable (d13) | | |
| 14 | 3.509 | 1.153 | 1.487 | 70.23 |
| 15 | −3.509 | 0.240 | | |
| 16 | 2.694 | 1.507 | 1.487 | 70.23 |
| 17 | −2.193 | 0.280 | 1.959 | 17.47 |
| 18 | −8.063 | 0.984 | | |
| 19 | ∞ | 0.380 | 1.516 | 64.14 |
| 20 | ∞ | 0.270 | 1.505 | 63.26 |
| Image plane | ∞ | | | |

Various data

| | wide angle end | telephoto end |
|---|---|---|
| d0 | 16 | 1.4 |
| d10 | 0.455 | 1.875 |
| d13 | 1.6 | 0.18 |

An observing optical system B has an arrangement as shown in FIG. 5A and FIG. 5B, and has the number of lenses smaller than those on the observing optical system A. Numerical data for the observing optical system B is shown below.

Numerical Example 8

Unit mm
(Observing optical system B)

Surface data

| Surface number | r | d | nd | vd |
|---|---|---|---|---|
| Object plane | ∞ | variable(d0) | | |
| 1 | ∞ | 0.202 | 1.883 | 40.76 |
| 2 | 0.45 | 0.290 | | |
| 3 | ∞ | 0.307 | 1.514 | 75.00 |
| 4 | ∞ | 0.060 | | |
| 5 | 11.03 | 1.003 | 1.652 | 58.55 |
| 6 | −0.911 | 0.030 | | |
| 7(Stop) | ∞ | variable(d7) | | |
| 8 | 1.342 | 0.303 | 1.804 | 46.57 |
| 9 | 1.74 | variable (d10) | | |
| 10 | 2.106 | 0.687 | 1.743 | 49.34 |
| 11 | −0.72 | 0.229 | 1.923 | 18.90 |
| 12 | −3.0 | 0.330 | | |
| 13 | ∞ | 0.320 | 1.516 | |
| 14 | ∞ | 0.400 | 1.504 | 60.00 |
| 15(Image plane) | | | | |

Various data

| | wide angle end | telephoto end |
|---|---|---|
| d0 | 11.6 | 2 |
| d7 | 0.6 | 0.15 |
| d10 | 0.18 | 0.63 |

In examples 1 to 5, an arrangement was made by combining the observing optical systems A and B and the illuminating optical systems A to F. Result thereof is shown below.

| | Ex. 1 | Ex. 2 | Ex. 3 | Ex. 4 | Ex. 5 |
|---|---|---|---|---|---|
| Illuminating optical system number | Three | Three | Three | Four | Four |

-continued

|  | Ex. 1 | Ex. 2 | Ex. 3 | Ex. 4 | Ex. 5 |
|---|---|---|---|---|---|
| Illuminating optical systems 12, 12a | Ill. A | Ill. A | Ill. D | Ill. D | Ill. A |
| Illuminating optical system 13 | Ill. B | Ill. C | Ill. E | Ill. F | Ill. E |
| Illuminating optical system 14 | Ill. B | Ill. C | Ill. E | Ill. F | Ill. C |
| (Illuminating optical system 12b) | — | — | — | Ill. D | — |
| Observing optical system 11 | Obs. A | Obs. B | Obs. A | Obs. B | Obs. A |
| rd1 | 3 | 3.2 | 3.5 | 2.5 | 3 |
| rd2 | 4.5 | 4.1 | 5 | 4.6 | 4.5 |
| rd3 | 4.95 | 4.5 | 5 | 4 | 5 |
| LI1 | 0.18 | 0.18 | 0.11 | 0.11 | 0.18 |
| LI2 | 0.76 | 1.00 | 0.63 | 0.42 | 0.63 |
| LI3 | 0.76 | 1.00 | 0.63 | 0.42 | 1.00 |
| w(wide) | 80.2 | 66.5 | 80.2 | 66.5 | 80.2 |
| w(tele) | 45.5 | 56.7 | 45.5 | 56.7 | 45.5 |
| θ1 | 46.2 | 46.2 | 41.9 | 41.9 | 46.2 |
| θ2 | 39.7 | 42.6 | 38.0 | 39.8 | 38.0 |
| θ3 | 39.7 | 42.6 | 38.0 | 39.8 | 42.6 |

Wherein, "Ill." denotes "Illuminating optical system", "Obs." denotes "Observing optical system".

Values corresponding to conditional expressions for examples 1 to 5 are shown below.

Conditional Expressions $$rd1/rd3 \quad (1)$$

$$rd1/rd2 \quad (2)$$

$$(rd2^2 \times LI1)/(rd1^2 \times LI2) \quad (3)$$

$$(rd3^2 \times LI1)/(rd1^2 \times LI3) \quad (4)$$

$$w(wide)/w(tele) \quad (5)$$

$$\theta1/\theta2 \quad (6)$$

$$\theta1/\theta3 \quad (7)$$

| Expression | Ex. 1 | Ex. 2 | Ex. 3 | Ex. 4 | Ex. 5 |
|---|---|---|---|---|---|
| (1) | 0.667 | 0.780 | 0.700 | 0.543 | 0.667 |
| (2) | 0.606 | 0.711 | 0.700 | 0.625 | 0.600 |
| (3) | 0.549 | 0.303 | 0.346 | 0.864 | 0.661 |
| (4) | 0.665 | 0.365 | 0.346 | 0.653 | 0.512 |
| (5) | 1.76 | 1.17 | 1.76 | 1.17 | 1.76 |
| (6) | 1.16 | 1.08 | 1.10 | 1.05 | 1.22 |
| (7) | 1.16 | 1.08 | 1.10 | 1.05 | 1.08 |

"Ex." denotes "Example."

Figure 6:
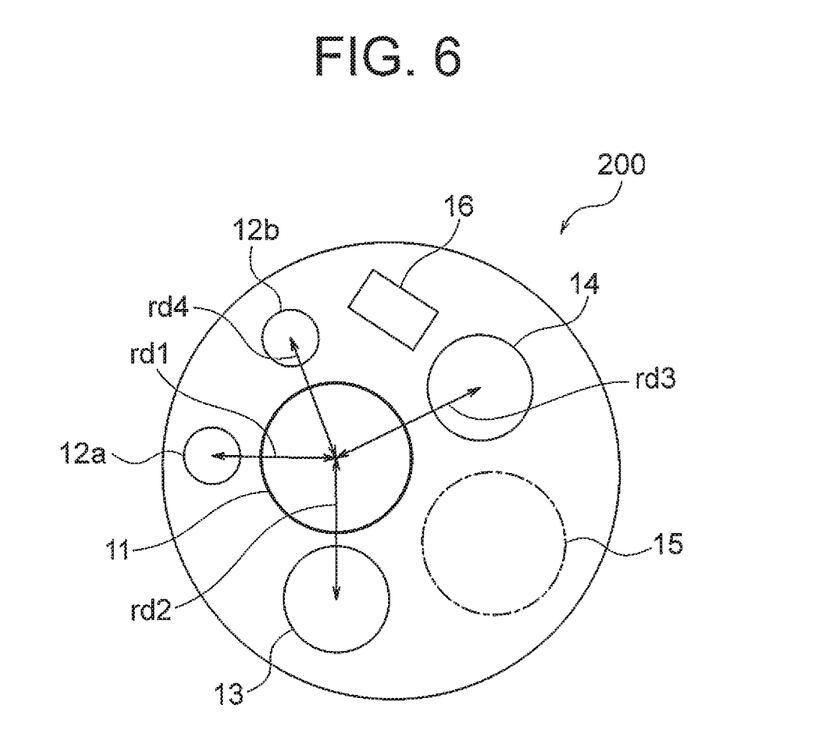
FIG. 6 is a diagram showing an arrangement of a front-end portion of an endoscope 200 according to a second embodiment.

Furthermore, another embodiment will be described below. FIG. 6 is a diagram showing an arrangement of a front-end portion of an endoscope 200 according to the another embodiment. Here, two illuminating optical systems 12a and 12b nearest to the observing optical system 11 are disposed. The two illuminating optical systems 12a and 12b correspond to the first illuminating optical system. Moreover, the illuminating optical systems 12a and 12b have the same arrangement. Therefore, relationships rd1=rd4, LI1=LI4, and θ1=θ4 are established.

It is shown below that in the present embodiment, it is possible to make the brightness uniform at the time of proximity observation. Numerical values shown below are angle-brightness characteristics at the time when a position of a center of a lens nearest to object in the observing optical system 11 is let to be a point of origin, when a distance between the observing optical system 11 and an object which is a flat surface is 2 mm. Numerical values are indicated upon standardizing such that the maximum illumination intensity in an X-direction and a Y-direction becomes 1.

| Angle | Ex. 1 | Ex. 2 | Ex. 3 | Ex. 4 | Ex. 5 |
|---|---|---|---|---|---|
| (Values in X-direction) | | | | | |
| −56.7 | — | 0.67 | — | 0.84 | — |
| −55 | — | 0.69 | — | 0.82 | — |
| −50 | — | 0.74 | — | 0.73 | — |
| −45.5 | 0.33 | 0.75 | 0.30 | 0.65 | 0.40 |
| −45 | 0.33 | 0.75 | 0.30 | 0.64 | 0.40 |
| −40 | 0.33 | 0.74 | 0.29 | 0.57 | 0.39 |
| −35 | 0.32 | 0.72 | 0.28 | 0.52 | 0.39 |
| −30 | 0.32 | 0.69 | 0.27 | 0.49 | 0.38 |
| −25 | 0.32 | 0.67 | 0.26 | 0.46 | 0.37 |
| −20 | 0.32 | 0.64 | 0.26 | 0.44 | 0.37 |
| −15 | 0.32 | 0.62 | 0.26 | 0.44 | 0.37 |
| −10 | 0.33 | 0.59 | 0.26 | 0.44 | 0.38 |
| −5 | 0.34 | 0.57 | 0.26 | 0.44 | 0.38 |
| 0 | 0.35 | 0.56 | 0.27 | 0.46 | 0.39 |
| 5 | 0.37 | 0.54 | 0.28 | 0.48 | 0.41 |
| 10 | 0.40 | 0.54 | 0.29 | 0.51 | 0.44 |
| 15 | 0.43 | 0.53 | 0.32 | 0.54 | 0.47 |
| 20 | 0.48 | 0.54 | 0.36 | 0.58 | 0.51 |
| 25 | 0.53 | 0.55 | 0.41 | 0.64 | 0.56 |
| 30 | 0.61 | 0.57 | 0.48 | 0.70 | 0.63 |
| 35 | 0.70 | 0.61 | 0.59 | 0.78 | 0.71 |
| 40 | 0.83 | 0.66 | 0.74 | 0.87 | 0.84 |
| 45 | 0.98 | 0.75 | 0.97 | 0.96 | 0.98 |
| 45.5 | 1.00 | 0.76 | 1.00 | 0.97 | 1.00 |
| 50 | — | 0.87 | — | 1.00 | — |
| 55 | — | 0.98 | — | 0.92 | — |
| 56.7 | — | 1.00 | — | 0.85 | — |
| (Values in Y-direction) | | | | | |
| −56.7 | — | 1.00 | — | 0.47 | — |
| −55 | — | 0.97 | — | 0.50 | — |
| −50 | — | 0.85 | — | 0.58 | — |
| −45.5 | 1.00 | 0.75 | 1.00 | 0.60 | 0.65 |
| −45 | 0.98 | 0.74 | 0.98 | 0.60 | 0.63 |
| −40 | 0.82 | 0.65 | 0.79 | 0.58 | 0.55 |
| −35 | 0.71 | 0.58 | 0.67 | 0.56 | 0.51 |
| −30 | 0.64 | 0.52 | 0.60 | 0.53 | 0.48 |
| −25 | 0.59 | 0.48 | 0.55 | 0.49 | 0.47 |
| −20 | 0.55 | 0.45 | 0.52 | 0.46 | 0.47 |
| −15 | 0.52 | 0.42 | 0.50 | 0.44 | 0.48 |
| −10 | 0.51 | 0.40 | 0.48 | 0.41 | 0.49 |
| −5 | 0.49 | 0.38 | 0.48 | 0.39 | 0.50 |
| 0 | 0.48 | 0.37 | 0.48 | 0.37 | 0.51 |
| 5 | 0.47 | 0.37 | 0.48 | 0.36 | 0.53 |
| 10 | 0.47 | 0.37 | 0.48 | 0.35 | 0.55 |
| 15 | 0.47 | 0.37 | 0.50 | 0.34 | 0.58 |
| 20 | 0.47 | 0.38 | 0.52 | 0.33 | 0.61 |
| 25 | 0.48 | 0.40 | 0.55 | 0.34 | 0.65 |
| 30 | 0.50 | 0.42 | 0.60 | 0.35 | 0.70 |
| 35 | 0.52 | 0.46 | 0.67 | 0.38 | 0.77 |
| 40 | 0.57 | 0.50 | 0.79 | 0.42 | 0.86 |
| 45 | 0.65 | 0.57 | 0.98 | 0.50 | 0.98 |
| 45.5 | 0.66 | 0.58 | 1.00 | 0.51 | 1.00 |
| 50 | — | 0.66 | — | 0.63 | — |
| 55 | — | 0.77 | — | 0.88 | — |
| 56.7 | — | 0.80 | — | 1.00 | — |

As described heretofore, according to the present invention, it is possible to provide an endoscope which enables to achieve a favorable light distribution in both the normal observation and the proximity observation.

Various embodiments of the present invention have been described above. However, the present invention is not restricted to the embodiments described above, and embodiments in which arrangements of these embodiments are combined appropriately without departing from the scope of the present invention are also in the category of the present invention.

As described heretofore, the endoscope according to the present invention is suitable for an endoscope which enables to achieve a favorable light distribution in both the normal observation and the proximity observation.

The present invention shows an effect that it is possible to provide an endoscope which enables to achieve a favorable light distribution in both the normal observation and the proximity observation.

What is claimed is:

1. An endoscope, comprising:
an observing optical system having a magnified-observation function, which enables a proximity observation by approximating an object; and
at least three illuminating optical systems which are, a first illuminating optical system, a second illuminating optical system, and a third illuminating optical system, wherein
an amount of light of the first illuminating optical system which is at a distance nearest from the observing optical system, out of at least the three illuminating optical systems which are the first illuminating optical system, the second illuminating optical system, and the third illuminating optical system, is not more than half of an amount of light of the second illuminating optical system and the third illuminating optical system, and
the endoscope satisfies the following conditional expressions (1'), (2'), (3), (4), (6), and (7)

$$0.5 < rd1/rd3 < 0.75 \quad (1')$$

$$0.5 < rd1/rd2 < 0.75 \quad (2')$$

$$0.3 < (rd2^2 \times LI1)/(rd1^2 LI2) < 1.2 \quad (3)$$

$$0.3 < (rd3^2 \times LI1)/(rd1^2 \times LI3) < 1.2 \quad (4)$$

$$1.05 < \theta1/\theta2 < 1.45 \quad (6)$$

$$1.05 < \theta1/\theta3 < 1.45 \quad (7)$$

where,
rd1 denotes a distance between a center of a lens disposed nearest to object in the observing optical system and a center of a lens disposed nearest to object in the first illuminating optical system,
rd2 denotes a distance between the center of the lens disposed nearest to object in the observing optical system and a center of a lens disposed nearest to object in the second illuminating optical system,
rd3 denotes a distance between the center of the lens disposed nearest to object in the observing optical system and a center of a lens disposed nearest to object in the third illuminating optical system,
here,
the distance rd1 is a value smaller than the distances rd2 and rd3,
LI1 denotes the amount of light of the first illuminating optical system,
LI2 denotes the amount of light of the second illuminating optical system,
LI3 denotes the amount of light of the third illuminating optical system,
θ1 denotes an angle when an amount of light emerged in a 0° direction is let to be 1 becomes 0.3 with respect to light-distributed emerged from the first illuminating optical system,
θ2 denotes an angle when an amount of light emerged in the 0° direction is let to be 1 becomes 0.3 with respect to light-distributed emerged from the second illuminating optical system, and
θ3 denotes an angle when an amount of light emerged in the 0° direction is let to be 1 becomes 0.3 with respect to light-distributed emerged from the third illuminating optical system.

2. The endoscope according to claim 1, wherein the endoscope satisfies the following conditional expression (5)

$$1.1 < w(\text{wide})/w(\text{tele}) < 3 \quad (5)$$

where,
w(wide) denotes an angle of view at the time of normal observation of the observing optical system, and
w(tele) denotes an angle of view at the time of proximity magnified observation of the observing optical system.

* * * * *